United States Patent
Abt et al.

(10) Patent No.: US 11,096,707 B2
(45) Date of Patent: Aug. 24, 2021

(54) ACTUATION HANDLE

(71) Applicant: Alcon Inc., Fribourg (CH)

(72) Inventors: Niels Alexander Abt, Winterthur (CH); Reto Grueebler, Greifensee (CH); Timo Jung, Winterthur (CH); Niccolo Maschio, Winterthur (CH)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/709,544

(22) Filed: Dec. 10, 2019

(65) Prior Publication Data

US 2020/0187970 A1 Jun. 18, 2020

Related U.S. Application Data

(60) Provisional application No. 62/778,444, filed on Dec. 12, 2018.

(51) Int. Cl.
*A61B 17/29* (2006.01)
*A61B 17/30* (2006.01)

(52) U.S. Cl.
CPC .. *A61B 17/2909* (2013.01); *A61B 2017/2918* (2013.01); *A61B 2017/305* (2013.01)

(58) Field of Classification Search
CPC ...... A61F 9/007; A61F 9/00736; A61B 17/29; A61B 17/30; A61B 17/2909; A61B 2017/2918; A61B 2017/305
See application file for complete search history.

(56) References Cited

U.S. PATENT DOCUMENTS

| 6,391,046 | B1 | 5/2002 | Overaker |
| 6,482,198 | B1 | 11/2002 | Overaker et al. |
| 6,488,695 | B1 | 12/2002 | Hickingbotham |
| 8,012,146 | B2 | 9/2011 | Hickingbotham |
| 8,187,293 | B2 | 5/2012 | Kirchhevel |
| 9,149,389 | B2 | 10/2015 | Scheller |

(Continued)

FOREIGN PATENT DOCUMENTS

| JP | 5568016 B2 | 8/2014 |
| WO | WO0230302 A1 | 4/2002 |

(Continued)

OTHER PUBLICATIONS

Alcon Vitreoretinal Product Catalog, Section "Hand-Held Instrumentation", copyright 2008; Nov. 2009 Update, pp. 39-52.

*Primary Examiner* — George J Ulsh

(57) ABSTRACT

Certain embodiments provide a surgical instrument comprising surgical instrument comprising an device having a functional end and a main handle comprising a distal end coupled to the device. The surgical instrument further comprises an actuation handle insert comprising a number of first rolling components and an actuation tube coupled to the actuation handle insert, wherein the functional end of the device at least partially extends outside of the actuation tube when the device is deactivated. The surgical instrument further comprises levers comprising second rolling components. The surgical instrument further comprises a plurality of rolling elements, wherein each of the rolling elements is placed between one of the second rolling components and one of the first rolling components and pressing one or more of the levers pushes the actuation handle insert forward relative to the device, causing the actuation tube to transition the device from the deactivated state to an activated state.

17 Claims, 6 Drawing Sheets

(56) References Cited

U.S. PATENT DOCUMENTS

| | | |
|---|---|---|
| 9,173,772 B1 | 11/2015 | Scheller |
| 9,226,762 B2 | 1/2016 | Scheller |
| 9,247,951 B1 | 2/2016 | Scheller |
| 9,428,254 B1 | 8/2016 | Scheller |
| 9,480,598 B2 | 11/2016 | Clauson |
| 9,782,189 B2 | 10/2017 | Scheller |
| 9,795,506 B2 | 10/2017 | Scheller |
| 2001/0056286 A1 | 12/2001 | Etter |
| 2003/0171762 A1 | 9/2003 | Forchette |
| 2003/0195539 A1 | 10/2003 | Attinger |
| 2006/0089661 A1 | 4/2006 | Dodge |
| 2012/0150216 A1 | 6/2012 | Hickingbotham |
| 2015/0173944 A1 | 6/2015 | Linsi |
| 2017/0079675 A1 | 3/2017 | Scheller |
| 2017/0086871 A1 | 3/2017 | Scheller |
| 2017/0156748 A1 | 6/2017 | Scheller |
| 2017/0361034 A1 | 12/2017 | Scheller |
| 2018/0000643 A1 | 1/2018 | Scheller |
| 2018/0014849 A1 | 1/2018 | Scheller |
| 2018/0193192 A1 | 7/2018 | Charles |
| 2018/0235594 A1 | 8/2018 | Scheller |
| 2019/0247229 A1 | 8/2019 | Abt |

FOREIGN PATENT DOCUMENTS

| | | |
|---|---|---|
| WO | WO2017066026 A1 | 4/2017 |
| WO | WO2017218161 A1 | 12/2017 |
| WO | WO2018017296 A1 | 1/2018 |
| WO | WO2018156341 A1 | 8/2018 |

ACTUATION HANDLE

TECHNICAL FIELD

The present disclosure relates generally to an actuation handle having an actuation mechanism including rolling elements on inclined ramps.

BACKGROUND

During certain surgical procedures (e.g., ophthalmic procedures) a surgeon is required to manipulate (e.g., remove, cut, peel, etc.) certain tissues within a body part by using forceps, scissors, etc. An example of such surgical procedures is the internal limiting membrane (ILM) removal and epiretinal membrane (ERM) removal for treating different macular surface diseases. During such procedures, a surgeon inserts the tip of a surgical instrument which, for example, functions as forceps, into a patient's eye globe and uses the forceps to grasp and peel the ILM. Certain designs are currently used for providing a surgical instrument with an actuation handle that allows a surgeon to close and open the jaws of the forceps or scissors, which are located at the tip of a surgical instrument. However, in certain cases, the existing actuation handles involve too many parts, are structurally complicated, and difficult to assemble.

BRIEF SUMMARY

The present disclosure relates generally to an actuation handle having an actuation mechanism including rolling elements on inclined ramps.

Certain embodiments disclosed herein provide a surgical instrument comprising a device comprising a functional end configured to be inserted into a body part and a main handle comprising a distal end coupled to a proximal end of the device. The surgical instrument further comprises an actuation handle insert comprising a proximal end that is movably coupled to the main handle, the actuation handle insert comprising a number of first rolling components. The surgical instrument further comprises an actuation tube coupled to a distal end of the actuation handle insert, wherein the functional end of the device at least partially extends outside of a distal end of the actuation tube when the device is in a deactivated state. The surgical instrument further comprises a plurality of levers comprising proximal ends configured to be coupled to the main handle, wherein the plurality of levers comprise a corresponding number of second rolling components. The surgical instrument further comprises a plurality of rolling elements, wherein each of the rolling elements is placed between one of the number of second rolling components and one of the number of first rolling components and pressing one or more levers of the plurality of levers causes the rolling elements to roll down on at least one of the corresponding number of first rolling components or second rolling components and push the actuation handle insert forward relative to the device, causing the actuation tube to transition the device from the deactivated state to an activated state.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide an actuation handle having an actuation mechanism including rolling elements on inclined ramps.

Figure 1:
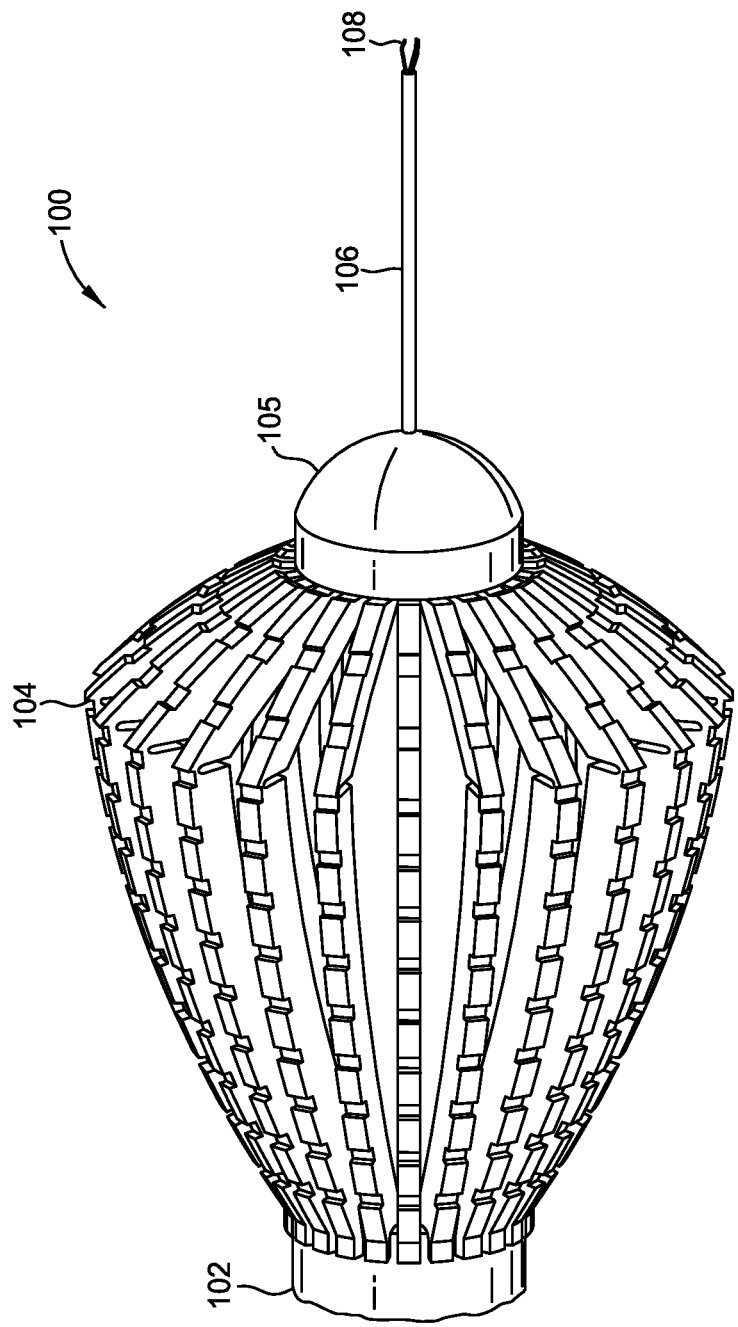
FIG. 1 illustrates an example of a surgical instrument with a prior art actuation handle.

FIG. 1 illustrates an example of a surgical instrument with a prior art actuation handle. As shown, the surgical instrument comprises a main handle ("handle") 102, a probe actuation handle ("actuation handle") 104, a tube housing 105, a probe actuation tube ("actuation tube or tube") 106, and a device, shown as forceps 108, at the tip of the probe. Actuation handle 104 is made from springy material having a memory, such as titanium, stainless steel or suitable thermoplastic. Tube 106 may be any suitable medical grade tubing, such as titanium, stainless steel, or suitable polymer and is sized so that forceps 108 reciprocate easily within. Forceps 108 are generally made from stainless steel or titanium, but other materials may also be used.

The surgical instrument of FIG. 1 is designed so that in use, when actuation handle 104 is in its relaxed stated, forceps 108 protrude or extend outside of the distal end of tube 106, which itself extends out of a tube housing 105. Squeezing actuation handle 104 moves or pushes tube housing 105 forward relative to handle 102. The forward movement of tube housing 105 is transferred to tube 106, causing tube 106 to slide forward over a distal portion of the jaws of forceps 108, thereby compressing together the jaws. By closing jaws of forceps 108, the surgeon is able to, for example, grasp and peel a tissue (e.g., ILM) within a body part. The amount of movement of tube 106 over forceps 108 can be controlled by varying the outer diameter of the actuation handle 104 in its relaxed state. In the example of FIG. 1, actuation handle 104 involves many parts, is structurally complicated, and can be difficult to assemble.

Accordingly, certain embodiments described herein relate to an actuation handle with an actuation mechanism including rolling elements on inclined ramps.

Figure 2:
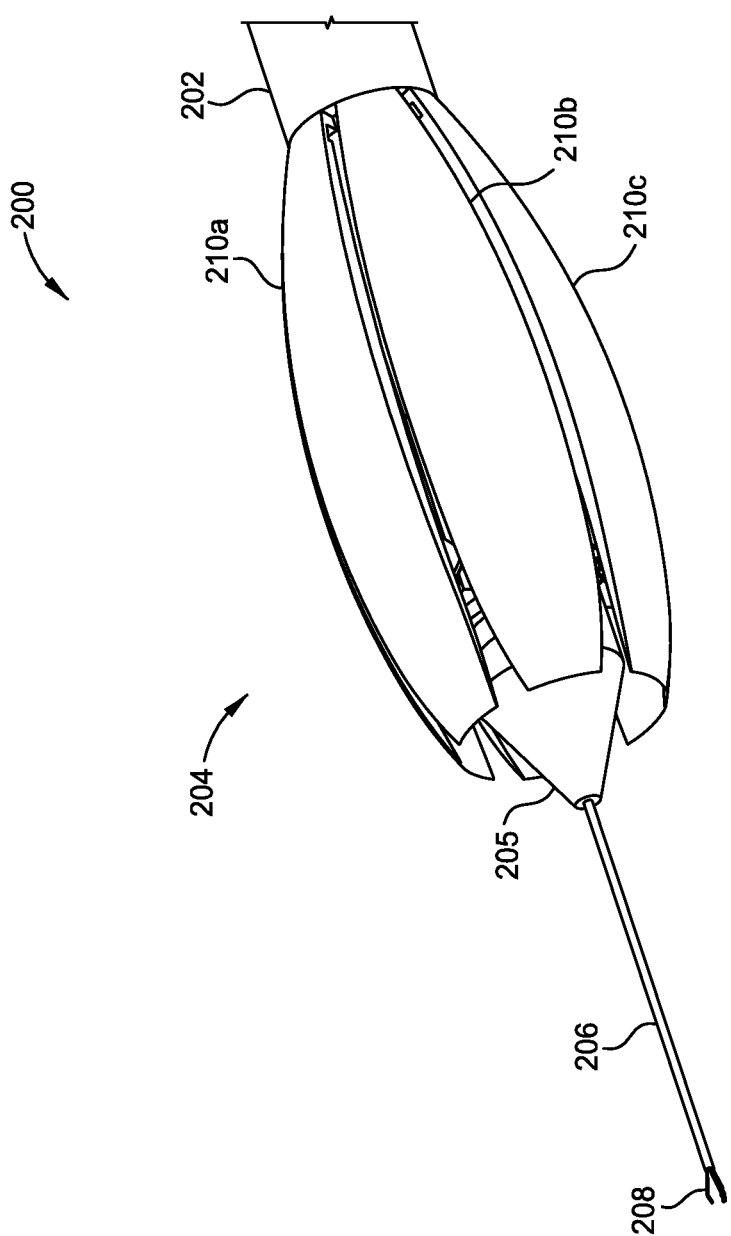
FIG. 2 illustrates an outside view of an example surgical instrument comprising an actuation element having levers, according to some embodiments.

FIG. 2 illustrates an outside view of an example surgical instrument 200 with a handle 202, an actuation handle 204, a tube housing 205, actuation tube 206, and device 208. As shown, actuation handle 204 comprises a number of levers 210 (e.g., 210a, 210b, 210c, etc.) that are configured to be pressed in order to move or push tube housing 205 forward relative to handle 202 and device 208. The forward movement of tube housing 205 is transferred to tube 206, causing tube 206 to slide forward and activate device 208, which, at its proximal end, is coupled to handle 202. Device 208 may be any surgical device that is shaped to fit in actuation tube 206 with a distal end that is referred to as a functional end (e.g., an active or movable end). For example, device 208 may be shaped as a needle with a functional end. The functional end of device 208 may comprise forceps, scissors, etc. with jaws or arms. The proximal end of device 208 is coupled to the distal end of handle 202's insert shown in FIG. 3. Device 208 is activated as a result of the forward movement of tube 206, which presses the jaws or arms of device 208 together. An activated device refers to a device whose jaws or arms are closed.

As shown in FIG. 2, surgical instrument 200 comprises six levers 210. However, a fewer or larger number of levers 210 may be used in other embodiments. Several techniques or mechanisms may be used for allowing levers 210 of actuation handle 204 to push tube housing 205 forward and activate device 208. FIGS. 3-6 illustrate a number of alternative mechanisms in more detail.

Figure 3:
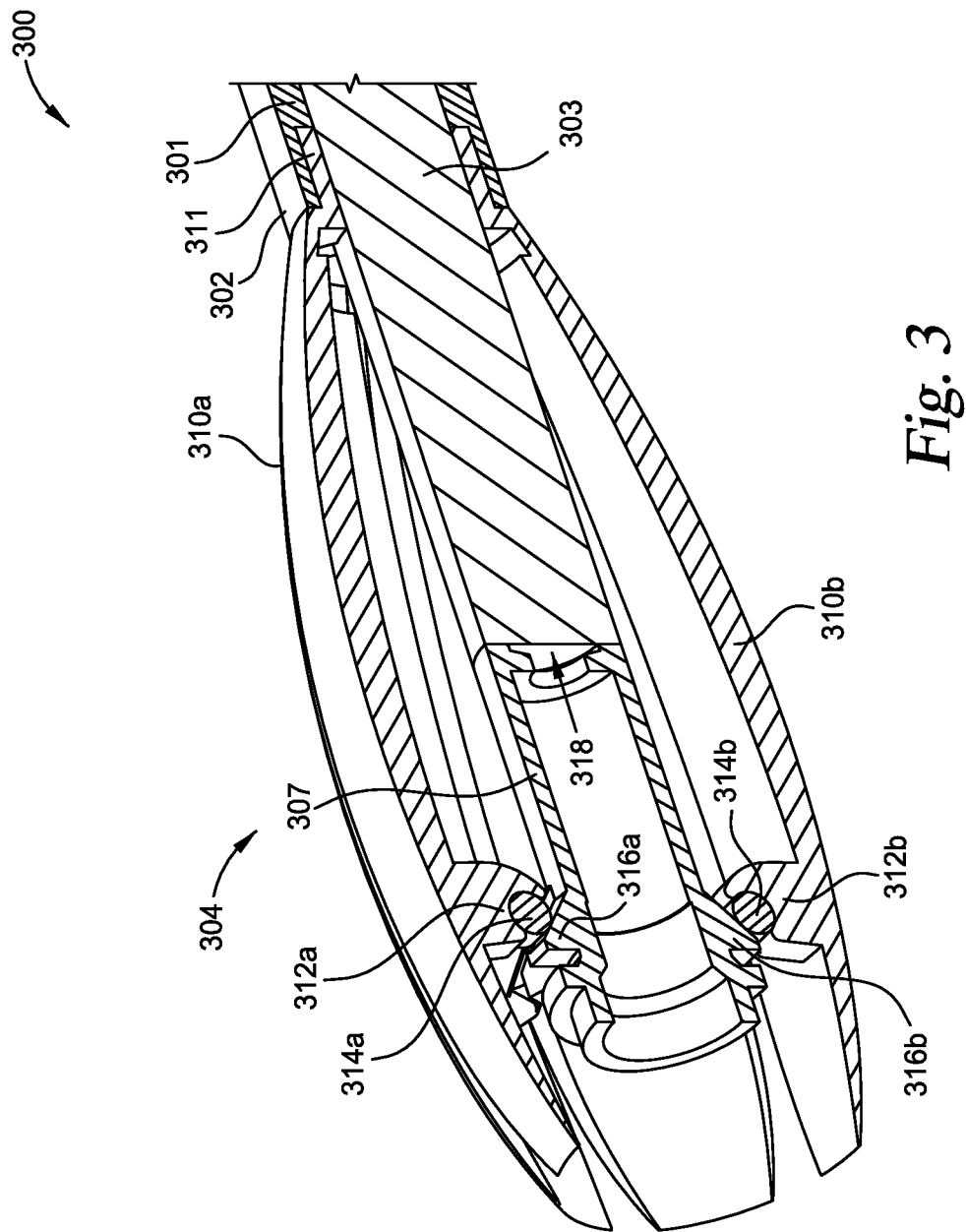
FIG. 3 illustrates an example cross-sectional view of a surgical instrument having an actuation handle with rolling element housings and ramps, according to some embodiments.

FIG. 3 illustrates a cross-sectional view of an example surgical instrument 300 comprising a handle 302 and an actuation handle 304 having a number of levers 310 such as levers 310a and 310b that are configured to interact with an actuation handle insert 307 through a number of rolling elements 314 such as rolling elements 314a and 314b. The tube housing, actuation tube, and device are not shown in FIGS. 3-6.

Figure 4:
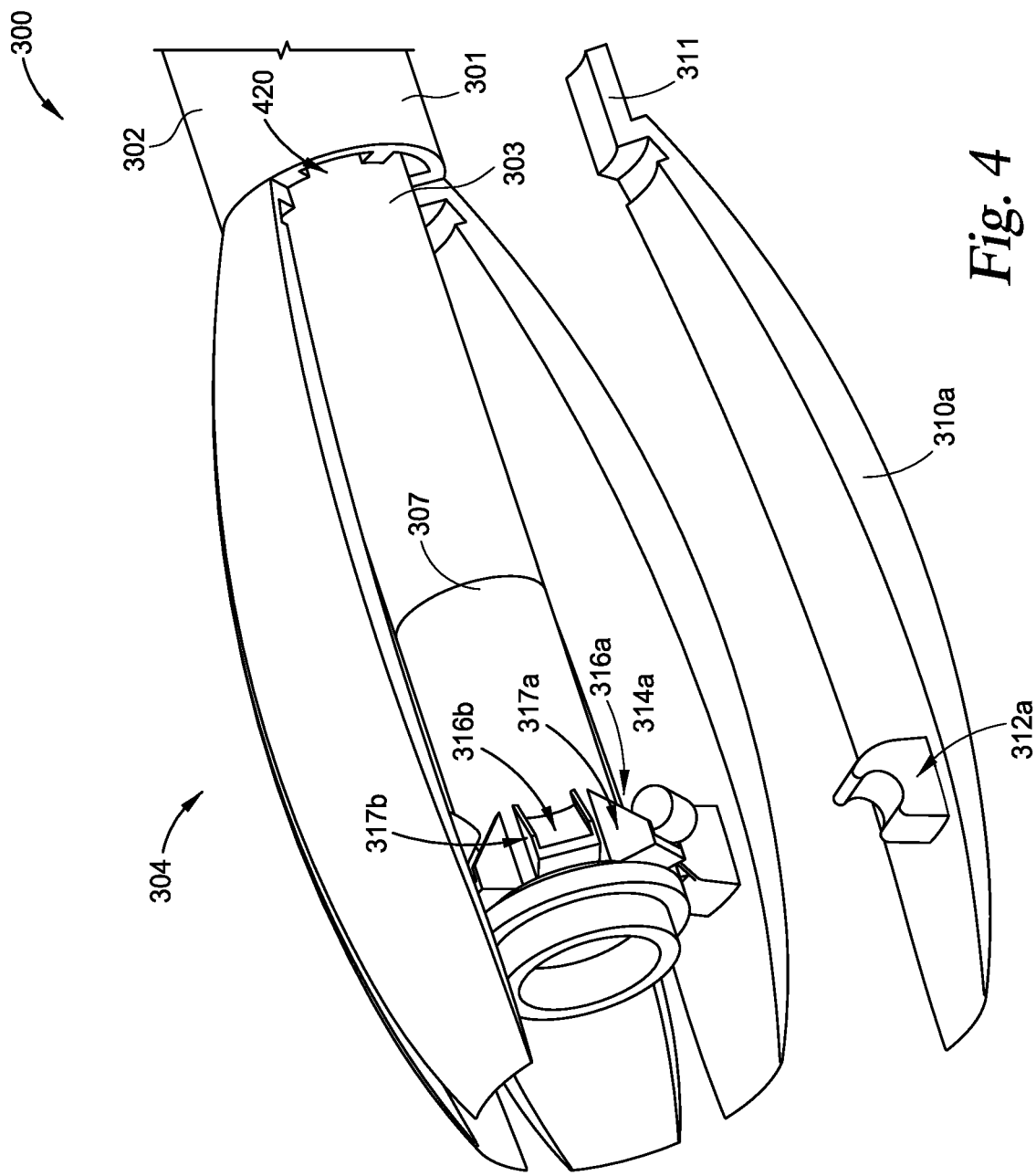
FIG. 4 illustrates the surgical instrument of FIG. 3 in more detail.

Handle 302 comprises a lever housing 301 and a handle insert 303. Lever housing 301 refers to a section of handle 302 that is shaped as a cylinder around handle insert 303 for the purpose of housing levers 310. More specifically, levers 310 comprise lever tails 311, which are held in place or housed by lever housing 301. As FIG. 4 shows in further detail, each lever tail 311 is inserted into a gap between the inner surface of lever housing 301 and the outer surface of handle insert 303. Handle insert 303, which is shaped as a cylinder, is coupled to actuation handle insert 307, which is also shaped as a cylinder with the same diameter as the diameter of handle insert 303. The device (not shown) extends through a tube housing (not shown), which is configured to be coupled to the distal end of actuation handle insert 307. The proximal end of the device further extends through actuation handle insert 307 and is coupled to the distal end 318 of handle insert 303 (or distal end of handle 302). As such, the device is stationary in that it does not move relative to handle insert 303.

In certain embodiments, actuation handle insert 307 and handle insert 303 are coupled together with a spring (not shown). Actuation handle insert 307 comprises a number of inclined ramps 316 on which rolling elements 314 are configured to roll and exert force, thereby, pushing actuation handle insert 307 forward, as described below.

Each lever 310 of actuation handle 304 comprises a rolling element housing 312 with a groove within which a rolling element 314 is placed for rolling. When viewed from a cross-sectional point of view, the groove has the shape of a half circle or a U. In the example of FIG. 3, rolling elements 314 are cylindrical. Each rolling element 314 is configured to roll on a respective inclined ramp 316 while being confined within a rolling element housing 312. The cross-sectional view of surgical instrument 300 in FIG. 3 illustrates only two ramps 316 of actuation handle insert 307. However, there are as many ramps 316 as levers 310. Also, a rolling element 314 is used in between each pair of ramp 316 and lever 310.

The actuation mechanism associated with actuation handle 304 involves a user, such as a surgeon, pressing one or more of levers 310 towards actuation handle insert 307, causing rolling elements 314 to roll down on corresponding ramps 316 while also exerting force on ramps 316. The force exerted by rolling elements 314 on ramps 316 pushes actuation handle insert 307 and the actuation tube (not shown) forward (e.g., towards the distal end of handle 300) relative to handle insert 307 and the device (not shown), thereby, resulting in activating the device attached to surgical instrument 300, such as described in relation to FIG. 2. In other words, the actuation mechanism associated with actuation handle 304 translates the force that is applied to levers 310 (e.g., on top of where rolling element housings 312 are located) into a horizontal movement of actuation element insert 307, which causes the device to activate. Causing the device to activate refers to causing the device to transitioning from a deactivated state to an activated state.

As described above, handle insert 303 is movably coupled to actuation handle insert 307 using a spring. As such, when actuation handle insert 307 is moved forward, the spring is extended and exerts opposite force on actuation handle insert 307 such that when the surgeon releases levers 310, actuation handle insert 307 moves back to its at-rest position. This causes the device to deactivate, which refers to a state where the jaws or arms of the device (e.g., forceps) are open.

In certain embodiments, rolling elements 314 and rolling element housings 312 are made from materials that would reduce friction between rolling elements 314 and rolling element housings 312 and enable rolling elements 314 to easily roll or rotate within rolling element housings 312. In other embodiments, a high friction between rolling elements 314 and ramps 316 may be desired to ensure that rolling elements 314 are able to actually roll on ramps 316 and push them forward instead of slipping on ramps 316. Although not shown, in certain embodiments, actuation handle 304 may be configured with a mechanism that causes all levers 310 to be pressed down, or move inwardly towards actuation handle insert 307, in response to one or more of levers 310 being pressed down. In certain embodiments, rolling elements 314 are made of rigid material, such as steel or ceramics. In certain embodiments, rolling element housings 312 are made of low friction material such as polyoxymethylene (POM) or polytetrafluoroethylene (PTFE). In certain embodiments, ramps 316 are made of polycarbonate, polyether ether ketone (PEEK), or similar material.

FIG. 4 illustrates the components of surgical instrument 300 of FIG. 3 in more detail. For example, lever 310a is shown separately, which comprises rolling element housing 312a. As shown, rolling element housing 312a comprises a half circle or u-shaped groove within which rolling element 314a is configured to roll. Because of its half circle or u-shaped groove, rolling element housing 312a allows rolling element 314a to only roll therein while prohibiting any movement of rolling element 314a in proximal and distal directions as well as limiting rolling element 314a's radial movement. A radial movement of rolling element 314a may refer to a movement or rotation of rolling element 314a around an axis of rotation that is perpendicular to an axis of rotation around which rolling element 314a rotates within rolling element housing 312a.

FIG. 4 also illustrates the ramp 316a on which rolling element 314a is configured to be placed. As shown, ramp 316a comprises side walls 317 that are configured to confine rolling element 314a from the sides in order to prevent any translational movement thereof. In certain embodiments, side walls 317 are placed at a distance from each other such that they are able to prevent any translational movement of rolling element 314a while also not pressing the sides of rolling element 314a to a point where rolling element 314a is not able to rotate due to excessive friction with side walls 317. Also shown is another ramp 316b from the top having side walls 317b.

In certain embodiments, a rolling element 314 may be placed between a rolling element housing 312 and a ramp 316 as a loose element. In such embodiments, the rolling element 314 is not coupled in any way to the rolling element housing 312. In certain other embodiments, a rolling element 314 comprises a bore that is inserted into a corresponding rolling element housing 312. In certain embodiments, the bore extends (e.g., through an axis) from the sides of rolling element 314 and is inserted into side walls 313 of the rolling element housing 312. In such embodiments, the rolling element 314 rotates around the bore. Using an element such as a bore, as discussed, holds the rolling element 314 in place and prohibits its undesired movements while also allowing it to rotate.

FIG. 4 further shows handle 302 with lever housing 301, having protrusions and grooves that create gaps between lever housing 301 and handle insert 303. An example of such a gap is shown as gap 420. As described above, such gaps are created for housing lever tails 311. For example, lever tail 311a is configured to be inserted into gap 420. In certain embodiments, lever tail 311a is press-fitted into gap 420.

Note that, in certain embodiments, instead of rolling element housings 312 being parts of levers 310 and ramps 316 being parts of actuation handle inserts 307, rolling element housings 312 are parts of actuation handle inserts 307 and ramps 316 are parts of levers 310. Also, note that instead of cylindrical rolling elements 314, in certain embodiments, spherical rolling elements may be used, in which case rolling element housing 312 may be modified accordingly.

Figure 5:
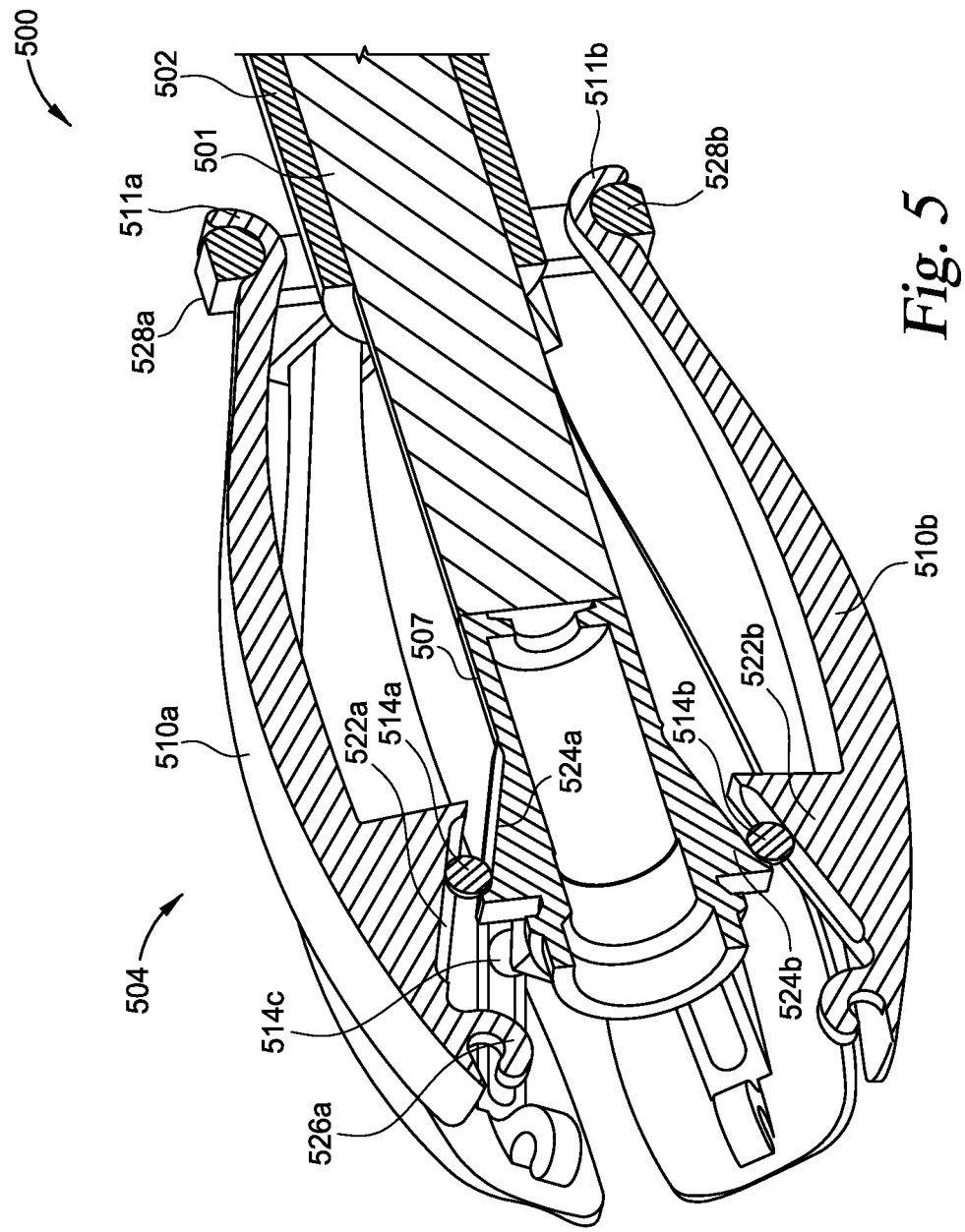
FIG. 5 illustrates an example cross-sectional view of a surgical instrument having an actuation handle with inner ramps and outer ramps, according to some embodiments.

FIG. 5 illustrates surgical instrument 500 using another example actuation mechanism in accordance with a particular embodiment. Surgical instrument 500 comprises an actuation handle 504 comprising levers 510 and actuation handle insert 507. As shown in FIG. 5, rolling elements 514 are configured to roll in between outer ramps 522 of levers 510 and inner ramps 524 of actuation handle insert 507. In FIG. 5, rolling elements 514 are spherical, such as bearing balls. As shown, a rolling element 514a is confined or entrapped by an outer ramp 522a from the top (or bottom, depending on how surgical instrument 500 is viewed) and an inner ramp 524a from the bottom (or top). An outer ramp 522 refers to a groove that is shaped as a channel with a starting point as well as an ending point, which act as stopping points for prohibiting any movement (e.g., longitudinal) of a rolling element 314 in proximal and distal directions beyond the starting and ending points of outer ramp 522. Inner ramps 524 are shaped and function similar to outer ramps 522.

The actuation mechanism associated with actuation handle 504 involves a surgeon pressing one or more of levers 510 towards actuation handle insert 507, causing rolling elements 514 to roll and exert force on inner ramps 524. The force exerted on inner ramps 524 is translated to actuation handle insert 507, thereby, pushing actuation handle insert 507 forward. Pushing actuation handle insert 507 forward results in activating a device (not shown) attached to surgical instrument 500, as described in relation to FIG. 2. Similar to surgical instrument 300, actuation handle insert 507 and handle insert 501 are also coupled together using a spring, in certain embodiments. As such, releasing or taking pressure off of levers 510 causes actuation handle insert 507 to retract and, therefore, deactivate the device.

At the tip of each lever 510 is a hook 526 through which an elastic band (not shown) such as a rubber band, may pass. More specifically, the elastic band runs circularly through all hooks 526 and stays under tension, thereby, pulling levers 510 towards actuation element insert 507. The elastic band is configured to restrict the movements of the tips of levers 510 away from actuation handle insert 507. This is because if a lever 510 moves too far away from actuation element insert 507, a corresponding rolling element 514 may no longer be confined between inner ramp 524 and outer ramp 522 and, therefore, drop. By using the elastic band, contact between levers 510, rolling elements 514, and actuation element insert 507 is ensured.

As shown, handle 502 of surgical instrument 500 comprises a number of elements 528. Lever tails 511, which are shaped like hooks, latch on to elements 825, which are configured to hold the lever tails 511 in place and prohibit any undesired movements. In FIG. 5, elements 825 are rectangle-shaped but in other embodiments elements 825 may be half circles, square-shaped, etc.

In certain embodiments, rolling elements 514 function as pivots such that the force that the tight elastic band exerts on the tips of levers 510 causes force to be exerted on lever tails 511 in an outward direction away from handle 502. This force causes lever tails 511 to be held in place, thereby, preventing lever tails 511 from being loose and moving inwardly towards handle 502.

Although in FIG. 5 rolling elements 514 are confined between a pair of inner and outer ramps, in certain embodiments, a rolling element cage may be used instead of one of the ramps. An example of a rolling cage is shown in FIG. 6.

Figure 6:
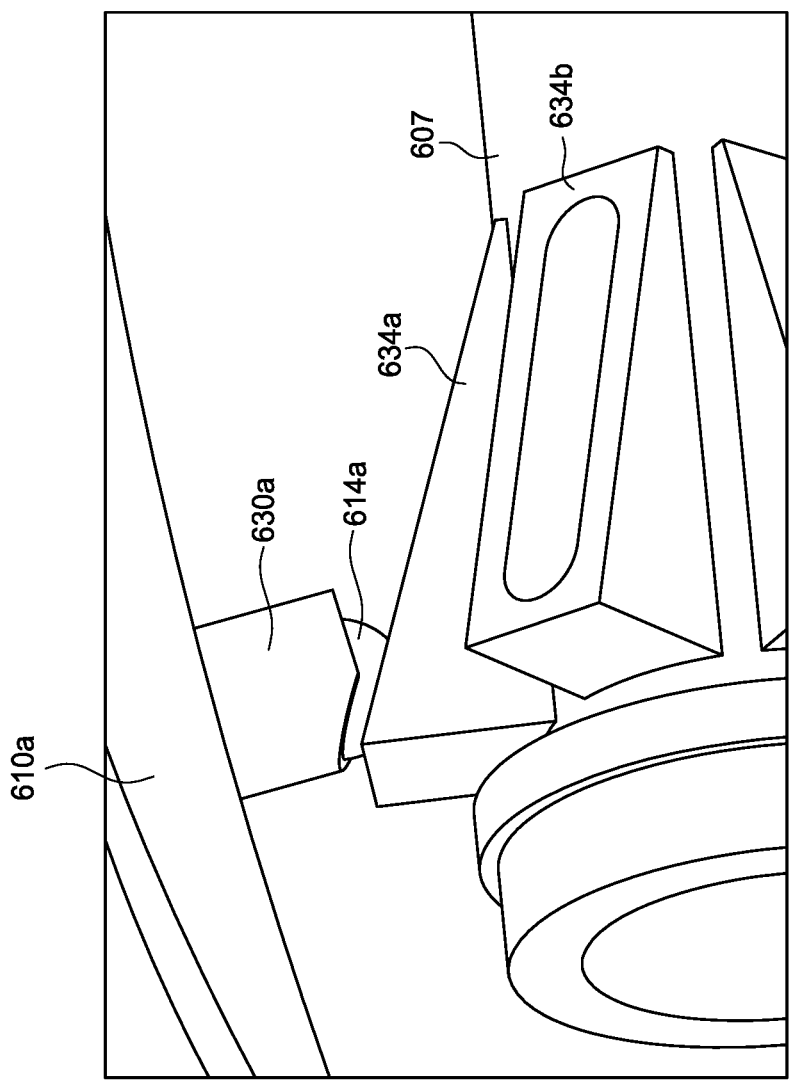
FIG. 6 illustrates an example cross-sectional view of a surgical instrument having an actuation handle with inner ramps and rolling element cages, according to some embodiments.

FIG. 6 illustrates a rolling element 614 confined by a rolling element cage 630. Rolling element 614 is configured to roll within rolling element cage 630 and on inclined ramp 634. As shown, rolling element cage 630 is a hollow cylindrical element whose tip is cut diagonally from one side as shown. This is to ensure that rolling element cage 630 does not make any contact with inclined ramp 634. Note that rolling housing elements 312, rolling element cages 630 and ramps 316, 522 and 524 may all be referred to as rolling components.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical instrument, comprising:
a device comprising a functional end configured to be inserted into a body part;
a main handle comprising a distal end coupled to a proximal end of the device;
an actuation handle insert comprising a proximal end that is movably coupled to the main handle, the actuation handle insert comprising a number of first rolling components;

an actuation tube coupled to a distal end of the actuation handle insert, wherein the functional end of the device at least partially extends outside of a distal end of the actuation tube when the device is in a deactivated state;

a plurality of levers comprising proximal ends configured to be coupled to the main handle, wherein the plurality of levers comprise a corresponding number of second rolling components; and a plurality of rolling elements, wherein:

each of the rolling elements is placed between one of the number of second rolling components and one of the number of first rolling components; and pressing one or more levers of the plurality of levers causes the rolling elements to roll down on at least one of the corresponding number of first rolling components or second rolling components and push the actuation handle insert forward relative to the device, causing the actuation tube to transition the device from the deactivated state to an activated state;

each of the first rolling components comprises a ramp, on which one of the plurality of rolling elements is configured to roll;

each of the second rolling components comprises a rolling element housing; and the rolling element housing comprises a groove, within which the one of the plurality of rolling elements is configured to roll;

wherein the ramp comprises side walls, which are configured to confine the one of the plurality of rolling elements.

2. The surgical instrument of claim 1, wherein:
the functional end of the device comprises jaws or arms; and
causing the actuation tube to transition the device from the deactivated state to the activated state further comprises closing the jaws or arms.

3. The surgical instrument of claim 1, wherein the plurality of rolling elements are cylindrical.

4. The surgical instrument of claim 1, wherein the groove is u-shaped or shaped as a half-circle.

5. The surgical instrument of claim 1, wherein the rolling element housing prohibits a radial movement of the one of the plurality of rolling elements.

6. A surgical instrument, comprising:
a device comprising a functional end configured to be inserted into a body part;
a main handle comprising a distal end coupled to a proximal end of the device:
an actuation handle insert comprising a proximal end that is movably coupled to the main handle, the actuation handle insert comprising a number of first rolling components;
an actuation tube coupled to a distal end of the actuation handle insert, wherein the functional end of the device at least partially extends outside of a distal end of the actuation tube when the device is in a deactivated state;
a plurality of levers comprising proximal ends configured to be coupled to the main handle, wherein the plurality of levers comprise a corresponding number of second rolling components; and
a plurality of rolling elements, wherein:
each of the rolling elements is placed between one of the number of second rolling components and one of the number of first rolling components; and
pressing one or more levers of the plurality of levers causes the rolling elements to roll down on at least one of the corresponding number of first rolling components or second rolling components and push the actuation handle insert forward relative to the device, causing the actuation tube to transition the device from the deactivated state to an activated state;

each of the first rolling components comprises a ramp, on which one of the plurality of rolling elements is configured to roll;

each of the second rolling components comprises a rolling element housing; and the rolling element housing comprises a groove, within which the one of the plurality of rolling elements is configured to roll;

wherein the ramp comprises a protrusion at its bottom for limiting a movement of the one of the plurality of rolling elements.

7. The surgical instrument of claim 6, wherein:
the functional end of the device comprises jaws or arms; and
causing the actuation tube to transition the device from the deactivated state to the activated state further comprises closing the jaws or arms.

8. The surgical instrument of claim 6, wherein the plurality of rolling elements are cylindrical.

9. The surgical instrument of claim 6, wherein the groove is u-shaped or shaped as a half-circle.

10. The surgical instrument of claim 6, wherein the rolling element housing prohibits a radial movement of the one of the plurality of rolling elements.

11. A surgical instrument, comprising:
a device comprising a functional end configured to be inserted into a body part;
a main handle comprising a distal end coupled to a proximal end of the device:
an actuation handle insert comprising a proximal end that is movably coupled to the main handle, the actuation handle insert comprising a number of first rolling components;
an actuation tube coupled to a distal end of the actuation handle insert, wherein the functional end of the device at least partially extends outside of a distal end of the actuation tube when the device is in a deactivated state;
a plurality of levers comprising proximal ends configured to be coupled to the main handle, wherein the plurality of levers comprise a corresponding number of second rolling components; and
a plurality of rolling elements, wherein:
each of the rolling elements is placed between one of the number of second rolling components and one of the number of first rolling components; and
pressing one or more levers of the plurality of levers causes the rolling elements to roll down on at least one of the corresponding number of first rolling components or second rolling components and push the actuation handle insert forward relative to the device, causing the actuation tube to transition the device from the deactivated state to an activated state;
wherein:
each of the first rolling components comprises a first ramp, on which one of the plurality of rolling elements is configured to roll; and
each of the second rolling components comprises a second ramp, on which the one of the plurality of rolling elements is configured to roll.

12. The surgical instrument of claim 11, wherein:
the first ramp comprises a first groove that is shaped as a channel with a first starting point and a first ending point; and the second ramp comprises a second groove that is shaped as a channel with a second starting point and a second ending point.

13. The surgical instrument of claim 12, wherein the first starting point, the first ending point, the second starting point, and the second ending point limit longitudinal movements of the one of the plurality of rolling elements.

14. The surgical instrument of claim 11, wherein:
the functional end of the device comprises jaws or arms; and
causing the actuation tube to transition the device from the deactivated state to the activated state further comprises closing the jaws or arms.

15. The surgical instrument of claim 11, wherein the plurality of rolling elements are cylindrical.

16. The surgical instrument of claim 12, wherein the groove is u-shaped or shaped as a half-circle.

17. The surgical instrument of claim 11, wherein a rolling element housing prohibits a radial movement of the one of the plurality of rolling elements.

\* \* \* \* \*